(12) United States Patent  
Teasdale

(10) Patent No.: US 6,846,304 B2
(45) Date of Patent: Jan. 25, 2005

(54) SPECIMEN CUP HOLDER

(76) Inventor: Jamie Teasdale, 113 Pennwood Ave., Pittsburgh, PA (US) 15218

( * ) Notice: Subject to any disclaimer, the term of this patent is extended or adjusted under 35 U.S.C. 154(b) by 0 days.

(21) Appl. No.: 09/901,468

(22) Filed: Jul. 9, 2001

(65) Prior Publication Data

US 2002/0077610 A1 Jun. 20, 2002

Related U.S. Application Data

(60) Provisional application No. 60/216,592, filed on Jul. 7, 2000.

(51) Int. Cl.[7] .......................... A61M 1/00; A47J 45/07; B65D 53/00
(52) U.S. Cl. .................. 604/317; 604/322; 16/425; 220/759; 220/769
(58) Field of Search ............... 604/317–321; 16/422, 425; 220/752, 759, 768, 769; 206/524.5; 422/102

(56) References Cited

U.S. PATENT DOCUMENTS

| | | | | |
|---|---|---|---|---|
| 1,457,657 A | * | 6/1923 | Fahsbender | .................. 16/425 |
| 2,450,193 A | * | 9/1948 | Galliano | ...................... 294/27 |
| 3,304,112 A | * | 2/1967 | Elliott | .......................... 294/34 |
| 3,625,654 A | | 12/1971 | Van Duyne | ................. 422/102 |
| 3,811,136 A | | 5/1974 | Whitney et al. | ............... 4/110 |
| 4,126,246 A | * | 11/1978 | Galer | ......................... 220/304 |
| 4,528,703 A | | 7/1985 | Kraus | ......................... 4/144.2 |
| 5,060,317 A | | 10/1991 | Bertelsen | .................... 4/144.2 |
| 5,202,094 A | * | 4/1993 | Jones et al. | ................ 16/111.1 |
| 5,342,330 A | | 8/1994 | Kane et al. | ................. 604/329 |
| D384,243 S | | 9/1997 | Nicollet | ....................... D7/395 |
| 5,704,092 A | * | 1/1998 | Nicollet et al. | ........... 16/110 A |
| 6,000,100 A | * | 12/1999 | Montgelard | .................. 16/425 |
| 6,257,439 B1 | * | 7/2001 | Hsu | ............................. 16/425 |
| 6,318,776 B1 | * | 11/2001 | Lee | ............................ 220/759 |

* cited by examiner

Primary Examiner—Larry I. Schwartz
Assistant Examiner—C. L Anderson
(74) Attorney, Agent, or Firm—Blynn L. Shideler; Krisanne Shideler; BLK Law Group

(57) ABSTRACT

A urine collection device which includes a urine collection vessel and a handle which releasable grips a pouring edge of the urine collection vessel.

17 Claims, 3 Drawing Sheets

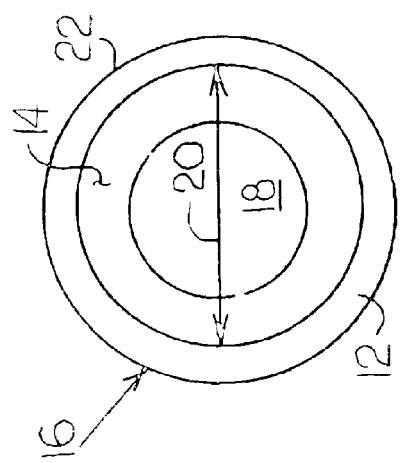
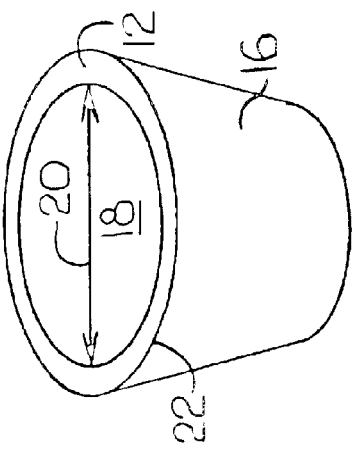
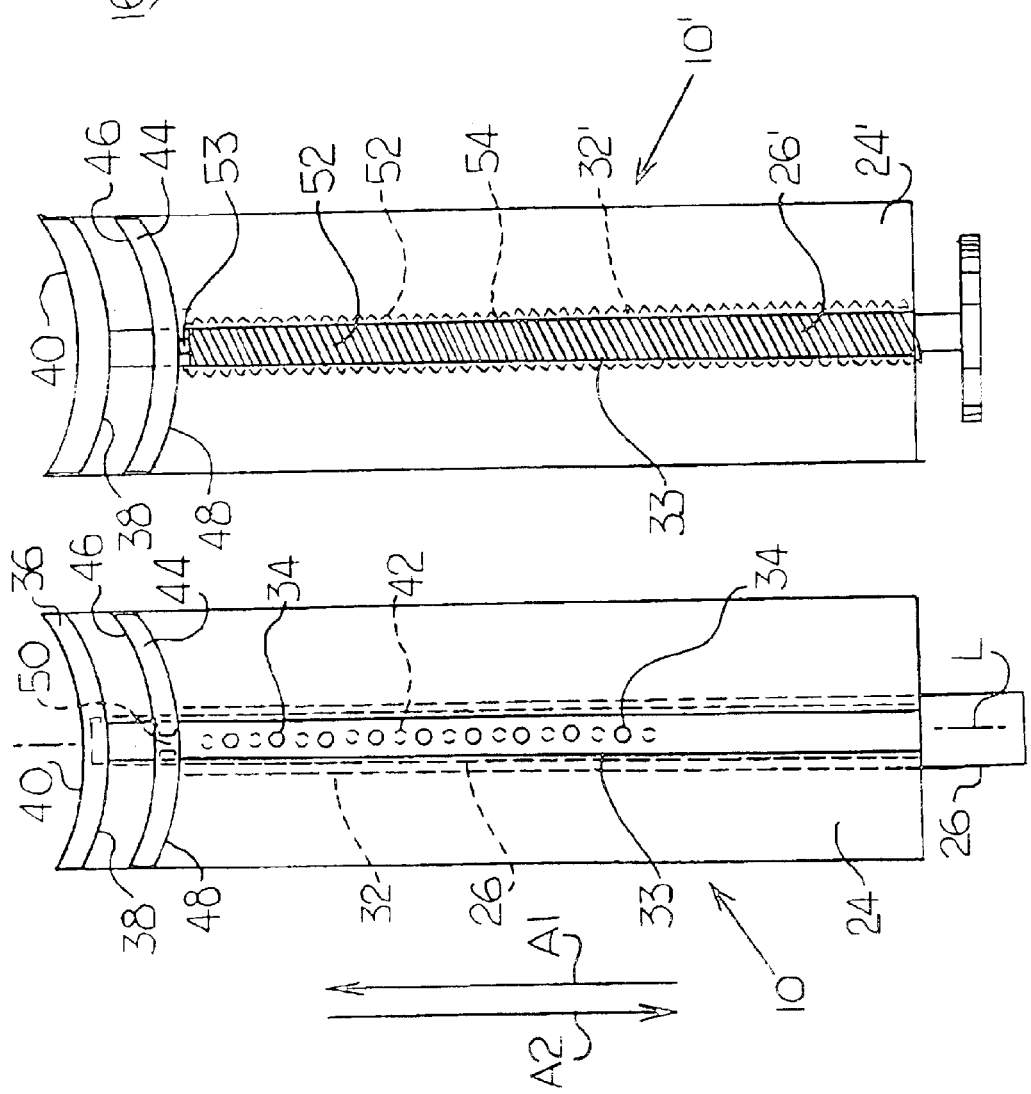

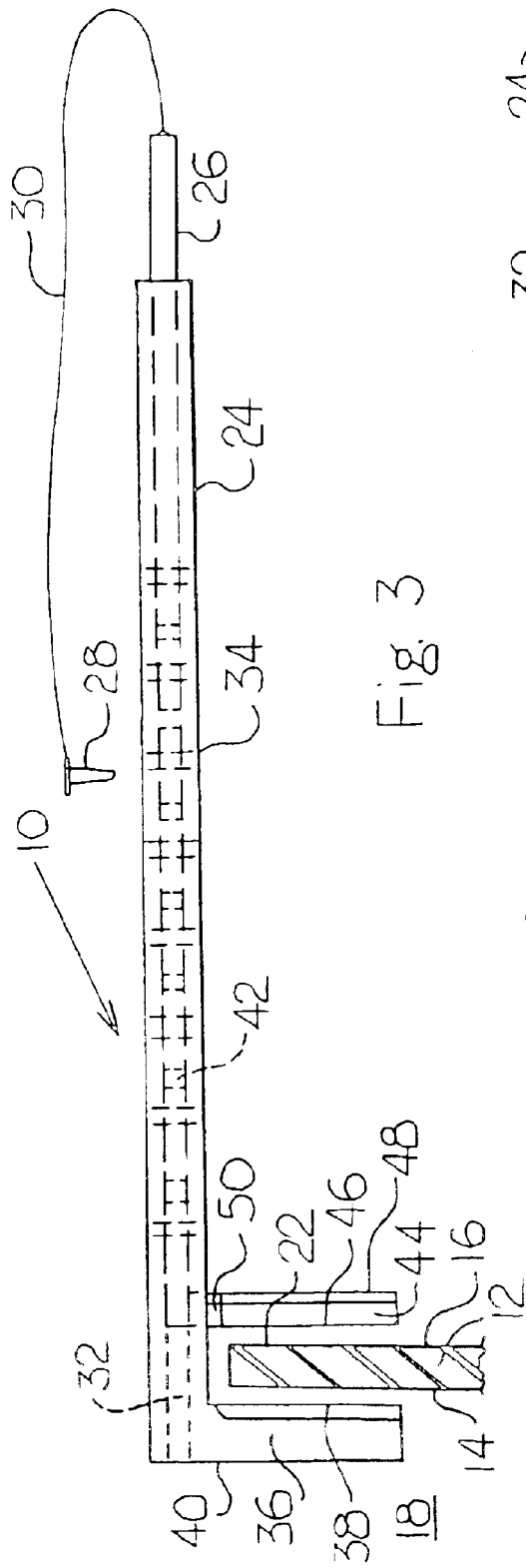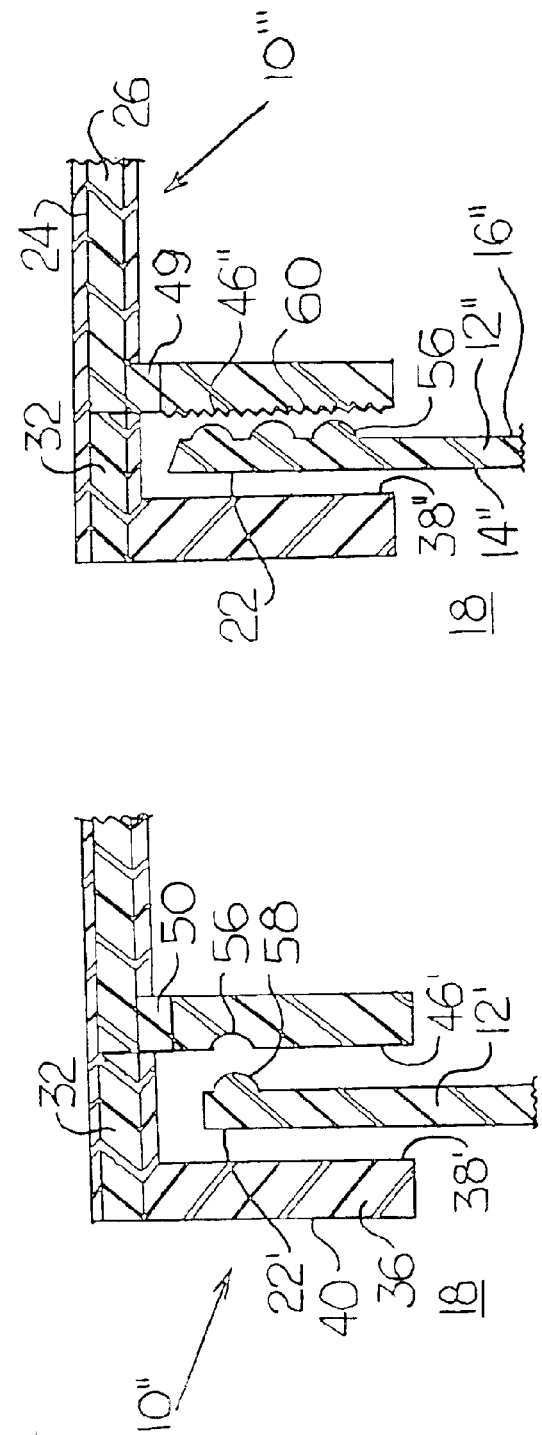

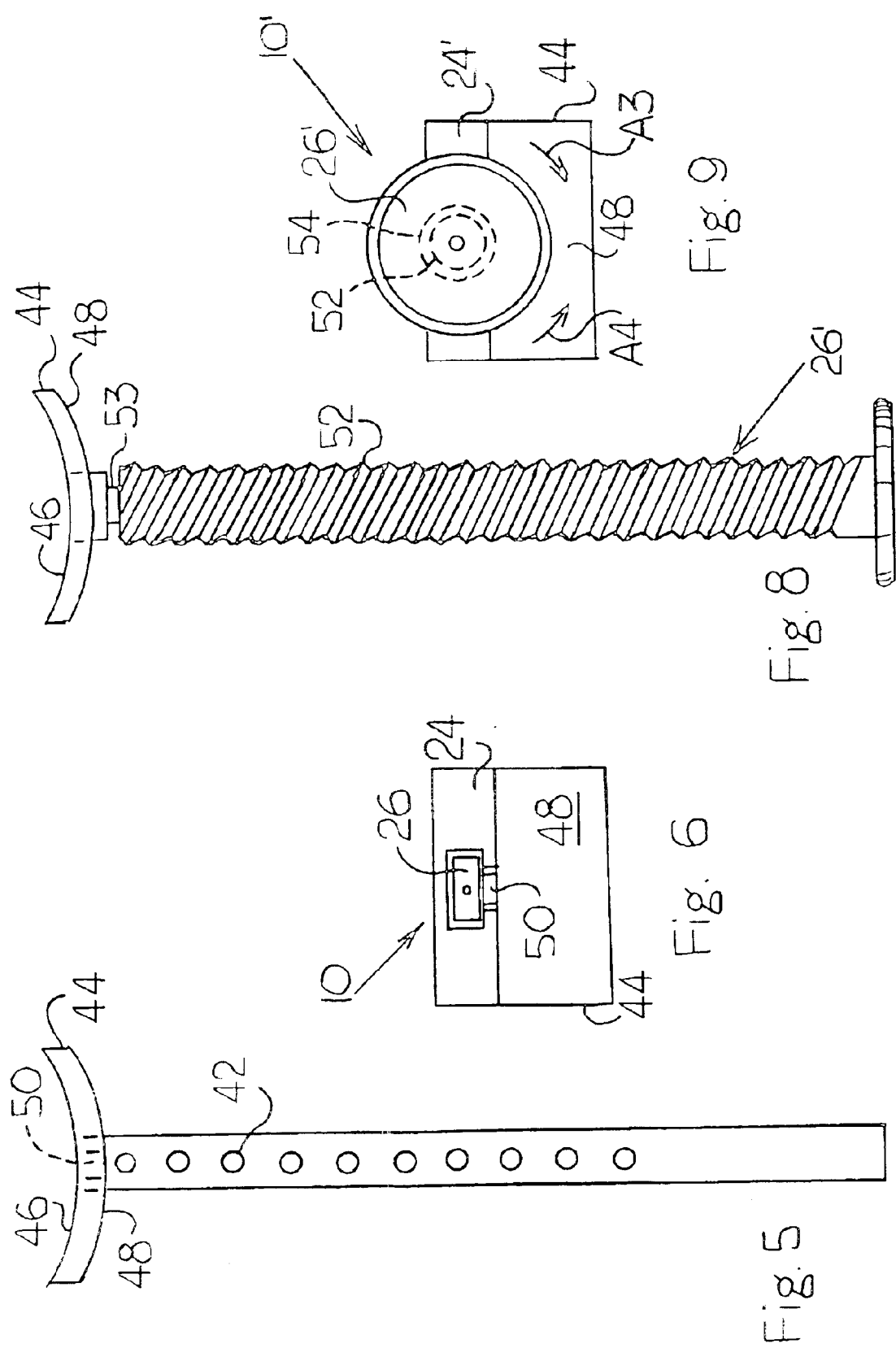

SPECIMEN CUP HOLDER

CROSS-REFERENCE TO RELATED APPLICATION

This application claims the benefit of earlier filed U.S. Provisional Patent Application Ser. No. 60/216,592, filed Jul. 7, 2000, entitled "Specimen Cup Holder."

BACKGROUND OF THE INVENTION

1. Field of the Invention

The present invention relates to medical devices and, more particularly, to a removable handle for a fluid specimen container.

2. Brief Description of the Prior Art

Doctors and other medical service providers routinely ask patients (or pets) for bodily fluids, such as urine samples. Urine samples are typically collected in a specimen container.

Standard specimen containers suffer from inherent design flaws. First, most specimen containers have a small inlet opening, making the process of filling the specimen container difficult. In some cases, the urine stream exiting the patient misses the inlet opening of the container and contacts the hand, fingers, or wrist of the patient. Given the physiological differences between men and women, and especially between men and pregnant women, men are generally more likely to successfully direct their urine stream into the inlet opening of the specimen container on the first attempt. However, physical conditions, such as blindness, arthritis, or obesity, may make the entire process equally difficult for both sexes.

The small fluid volume capacity of specimen containers also presents a problem. The fluid volume of most specimen containers is much smaller than the volume of the average bladder, requiring the patient to visually approximate the urine level in the specimen container. If the patient does not remove the specimen container from his or her urine stream in a timely fashion, the urine can overflow the specimen container and contact the hand, fingers, or wrist of the patient. As stated above, men are generally in a better position to visually determine the fluid level in the container. However, regardless of the gender or body shape of the patient, stopping the stream of urine at just the right time involves good eyesight, luck, and skill.

A third drawback of specimen containers relates to positive control of specimen containers during mandatory or routine drug testing. Under the current practice, the patient holds the specimen container and an observer watches the urine stream of the patient contact a bottom portion of the specimen container. Overlooking for the moment the embarrassment inflicted on the patient and the observer, allowing the patient to handle the specimen container presents the patient with the opportunity to alter the results of the drug test. For obvious reasons, ways of obtaining a false negative test will not be discussed.

To help alleviate the problems associated with filling specimen containers with urine or other liquids, various solutions have been proposed. For example, latex gloves prevent urine from contacting the skin of a patient. However, latex allergies are well documented, the gloves are not reusable, and urine can still flow along the exterior of the glove and contact the wrist, arm, or leg of a patient. Other approaches, such as those disclosed in U.S. Pat. Nos. 3,625,654; 5,060,317; and 5,342,330, are directed toward specimen containers having integrally formed handles, loosely connected handles, or pivotally connected handles. However, these approaches are also somewhat deficient. The most significant deficiency is that none of the devices are universally adapted to securely hold or grip specimen containers currently in wide use throughout the medical industry.

SUMMARY OF THE INVENTION

It is therefore an object of the present invention to provide a removable handle that securely holds many, if not all, standard plastic specimen containers used to collect bodily fluids.

One embodiment of the present invention generally includes a removable, adjustable handle for use with a specimen container. The specimen container generally includes a specimen container body having an inner wall and an outer wall, wherein the inner wall and the outer wall define a collection cavity, a fluid collection and retrieval opening, and a rim. The handle includes a first body member and a second body member. The first body member forms a first contact member which, in turn, has a first contact surface and an inner surface. The second body member forms a second contact member having a second contact surface and an outer surface. The first contact surface engages the inner wall of the specimen container body and the second contact surface engages the outer wall of the specimen container, removably securing the handle to the specimen container body.

One method of operation involves positioning the first contact member of the first body member adjacent to the rim formed by the specimen container body, with the first contact member protruding into the collection cavity and the first contact surface facing the inner wall of the specimen container body. The next step is positioning the second contact member of the second body member adjacent to the rim formed by the specimen container body, with the second contact surface of the second contact member facing the outer wall of the specimen container body. The next step is removably securing the handle to the rim of the specimen container body, such as by moving the second body member in a first direction until the first contact surface of the first contact member engages the inner wall of the specimen container body, and the second contact surface of the second contact member engages the outer wall of the specimen container body. The last step is removing the handle, such as by moving the second body member in a second, opposite direction.

This method of operation causes the rim of the specimen container body to be pinched, squeezed, or otherwise securely held between the first contact member and the second contact member. With the handle removably but securely attached to the specimen container body, the specimen container body and the fluid collection and retrieval opening can be oriented by a patient or a drug testing proctor via the handle without requiring physical contact with the specimen container. Moreover, because the handle is adjustable, the handle is adapted to fit many, if not all, specimen containers currently in widespread use.

These and other advantages of the present invention will be clarified in the Detailed Description of the Preferred Embodiments taken together with the attached drawings in which like reference numerals represent like elements throughout.

BRIEF DESCRIPTION OF THE DRAWINGS

FIG. 1 is a top view of a specimen container for collecting fluids;

FIG. 2 is a top perspective view of the specimen container shown in FIG. 1;

FIG. 3 is a side view of a first embodiment handle according to the present invention including a first body member, a second body member, and a locking member;

FIG. 4 is a bottom plan view of the first embodiment handle shown in FIG. 3 with the locking member removed;

FIG. 5 is a bottom view of the second body member shown in FIGS. 3 and 4;

FIG. 6 is an end view of the first embodiment handle shown in FIGS. 3 and 4;

FIG. 7 is a bottom plan view of a second embodiment handle according to the present invention including a first body member and a second body member;

FIG. 8 is a bottom plan view of the second body member shown in FIG. 7;

FIG. 9 is an end view of the second embodiment handle shown in FIG. 7;

FIG. 10 is cross-sectional side view of a third embodiment handle according to the present invention positioned adjacent a specimen container; and FIG. 11 is a cross-sectional side view of a fourth embodiment handle according to the present invention positioned adjacent a specimen container.

DETAILED DESCRIPTION OF THE PREFERRED EMBODIMENTS

The present invention generally includes a removable handle 10 for use with a specimen container. As shown in FIGS. 1 and 2, the specimen container generally includes a specimen container body 12 forming an inner wall 14 and an outer wall 16. The inner wall 14 and the outer wall 16 further define a collection cavity 18, a fluid collection and retrieval opening 20, and a rim 22.

One embodiment of a removable and adjustable handle according to the present invention is shown in FIGS. 3–6. A second embodiment is shown in FIGS. 7–9. A third embodiment is shown in FIG. 10. A fourth embodiment is shown in FIG. 11.

As shown in FIGS. 3–6, and with particular reference to FIG. 3, the first embodiment of a removable and adjustable handle 10 according to the present invention generally includes a first body member 24, a second body member 26, and a locking member 28 connected to the second body member 26 by a flexible chord 30. As shown in more detail in FIG. 4, the first body member 24 extends about a longitudinal axis L and forms an internal channel 32, a channel member orifice 33, guide holes 34, and a first contact member 36. The first contact member 36 forms a first contact surface 38 and an inner surface 40. The second body member 26, shown in detail in FIG. 5, forms locking holes 42 and a second contact member 44. The second contact member 44 forms a second contact surface 46 and an outer surface 48. The second contact member 44 is attached to the second body member by a channel member 50.

Referring again to FIG. 4, the second body member 26 is slidably received by the internal channel 32 formed by the first body member 24. The channel member 50 protrudes through the channel member orifice 33, allowing the attached second contact member 44 to move when the second body member 26 is moved in a first direction A1, or a second opposite direction A2, as indicated by the arrows. When the second body member 26 is moved in the first direction A1, the distance between the first and second contact members 36, 44 is reduced. This allows the first and second contact members 36, 44, and more specifically, the first and second contact surfaces 38, 46 engage the inner and outer walls 14, 16 of the specimen container body 12. Conversely, when the second body member 26 is moved in the second direction A2, the distance between the first and second contact members 36, 44 is increased. This allows the handle 10 to be removed from the specimen container body 12.

Referring again to FIG. 3, the locking member 28, in combination with the guide holes 34 and the locking holes 42, helps to keep the second body member 26 from moving after the first and second contact members 36, 44 engage the inner and outer walls 14, 16 of the specimen container body 12. The locking member can be cylindrical, squared, rectangular, triangular, tapered, wedge-shaped, or any other suitable shape. However, because the locking member 28 is received by the guide holes 34 formed by the first body member 24 and the locking holes 42 formed by the second body member 26 (when the guide holes 34 and the locking holes 42 are aligned), the locking member 28 should form the same exterior shape as the guide holes 34 and the locking holes 42.

The first body member 24, second body member 26, and the locking member 28 are preferably formed from a material, such as plastic (i.e., polyethylene or high density polyethylene), with plastic being preferred because it is inexpensive and disposable. However, reusable handles 10 (including the chord 30) should be made from a material that can be autoclaved or otherwise sterilized, such as surgical grade stainless steel or other suitable material. In general, any sturdy material is clearly contemplated.

Referring again to FIGS. 4 and 5, the first contact surface 38 and the second contact surface 46 are preferably arcuate in shape. An arcuate shape is preferred because a vast majority of the specimen containers currently being sold (FIG. 1) have a circular cross section when viewed through the fluid collection and retrieval opening 20. However, the first contact surface 38 and the second contact surface 46 can resemble any shape, so long as the first and second contact surfaces 38, 46 can engage the inner and outer walls 14, 16 of the specimen container body 12 and securely hold the specimen container body 12.

FIGS. 7–9 show a second embodiment handle 10' according to the present invention. The second embodiment handle 10' is similar to the first embodiment handle 10, with like reference numerals indicating like parts. However, as shown in detail in FIGS. 7 and 8, the second body member 26' forms external threads 52 which are received by internal threads 54 formed by the internal channel 32' of the first body member 24'. A 360° swivel joint 53 is positioned adjacent to the second contact member 44 and the threaded portion 52 of the second body member 26'. As shown in FIG. 9, as the second body member 26' is rotated in a first direction A3, the second body member 26' is threadedly advanced in the first body member 24' and the distance between the first contact member 36 and second contact member 44 is decreased. Conversely, if the second body member 26' is rotated in a second direction A4, the distance between the first contact member 36 and the second contact member 44 is decreased. This design eliminates the need for the locking members 28, the guide holes 34, and the locking holes 42, as illustrated in FIG. 3.

FIG. 10 shows a third embodiment handle 10" according to the present invention. As shown in this embodiment, the first and second contact surfaces 38', 46' can form notches 56 to accommodate threads 58 (for a screw-on type lid) formed adjacent the rim 22' of the specimen container body 12'. Similarly, as shown in FIG. 11, the first and second contact surfaces 38", 46" of a fourth embodiment handle 10'" can form scored sections 60 to provide a raised surface area to help increase friction between the first contact surface 38" and the interior wall 14" of the specimen container body 12" and between the second contact surface 46" and the outer wall 16' of the specimen container body 12".

In addition to being adjustable, an important aspect of this invention is that, shown generally in FIG. 3, the first contact member 36 and the second contact member 44 engage the inner wall 14 and the outer wall 16 of the specimen container body 12 securely but removably attaching the handle 10 to the specimen container (preferably adjacent the rim 22). Therefore, other types of handles or approaches, when used in connection with the specimen container, are clearly contemplated. An example is U.S. Des. Pat. No. 384,243, herein incorporated by reference, which discloses a removable handle for cooking utensils.

The invention has been described with reference to the preferred embodiment. Obvious modifications and alterations will occur to others upon reading and understanding the preceding detailed description. It is intended that the invention be construed as including all such modifications and alterations.

I claim:

1. A bodily fluid collection system comprising:
   a plastic specimen container for the collection and temporary retention of urine, the plastic specimen container comprising a plastic body that defines an inner wall, an outer wall, a single urine collection and retrieval opening defined by a rim;
   a handle having a first body member and a second body member, wherein the first body member defines a first contact member that defines a first contact surface and the second body member defines a second contact member that defines a second contact surface and;
   a releasable lock member, incorporated into the handle, that temporarily suspends opposed movement of the first body member and the second body member;
   wherein the first contact surface of the first contact member engages the inner wall of the plastic body and the second contact surface of the second contact member engages the outer wall of the plastic body to create a temporary clamp force that is maintained until the releasable lock member is disengaged.

2. The handle as claimed in claim 1, wherein the first body member and the second body member slide parallel to one another.

3. The handle as claimed in claim 1, wherein the first body member defines internal threads, and the second body member defines external threads, wherein an interaction of the internal threads and the external threads is the releasable lock member.

4. The handle as claimed in claim 1, wherein the first body member and the second body member slide parallel to one another and the releasable lock member is a pin removeably received in an aligned orifice defined by the first body member and the second body member.

5. The urine collection device as claimed in claim 1, wherein the second contact surface defines notches which accommodate threads positioned adjacent to the rim.

6. The urine collection device as claimed in claim 1, wherein the second contact surface defines scored sections which accommodate threads positioned adjacent to the rim.

7. A method to collect a urine with a handle and a specimen container, comprising the steps of:

a) providing a handle that comprises a first body member, a second body member that is movable with respect to the first body member, and a releasable lock member incorporated into the handle, wherein the first body member has a first contact member that defines a first contact surface and the second body member has a second contact member that defines a second contact surface;

b) providing a plastic specimen container comprising an inner wall, an outer wall, and a single urine collection and retrieval opening defined by a rim;

c) positioning the first contact surface of the first contact member adjacent to the inner wall of the plastic specimen container;

d) positioning the second contact member of the second body member adjacent to the outer wall of the plastic specimen container, opposite the first contact member;

e) compressing the plastic specimen container between the first contact member and the second contact member via the handle; and f) maintaining a compression force on the plastic specimen container via the releasable lock member.

8. The method as claimed in claim 7 further comprising the step of moving the second contact member in a first direction prior to the step of compressing the plastic specimen container between the first contact member and the second contact member via the handle.

9. The method as claimed in claim 7 further comprising the step of disengaging the releasable lock member after the step of maintaining a compression force on the plastic specimen container via the releasable lock member.

10. The method as claimed in claim 9 further comprising the step of removing the handle from the plastic specimen container.

11. A handle for use with a plastic specimen container, the handle comprising:
    a first body member that defines a first contact surface and a guide hole;
    a second body member that defines a second contact surface and a locking hole; and
    a removable lock member;
    wherein the first body member moves parallel to the second body member until the guide hole and locking hole are aligned with one another and the removable lock member is removably inserted into the guide hole the locking hole.

12. The handle as claimed in claim 11, wherein the first contact surface of the first contact member defines an arcuate shape.

13. The handle as claimed in claim 12, wherein the second contact surface of the second contact member defines an arcuate shape.

14. The handle as claimed in claim 11, wherein the second contact surface defines at least one notch.

15. The handle as claimed in claim 11, wherein the second contact surface defines a plurality of scored sections.

16. The urine collection device as claimed in claim 11, wherein the second contact surface defines notches which accommodate the threads positioned adjacent to the rim.

17. The urine collection device as claimed in claim 11, wherein the second contact surface defines scored sections which accommodate threads positioned adjacent to the rim.

\* \* \* \* \*